United States Patent
Spangenberg et al.

(12) 
(10) Patent No.: US 6,485,687 B1
(45) Date of Patent: Nov. 26, 2002

(54) THIN-LAYER CHROMATOGRAPHY APPARATUS

(76) Inventors: Bernd Spangenberg, Am Rittweg 10, D-77654 Offenburg (DE); Karl-Friedrich Klein, Allmendstrasse 35, D-61169 Friedberg (DE)

( * ) Notice: Subject to any disclaimer, the term of this patent is extended or adjusted under 35 U.S.C. 154(b) by 0 days.

(21) Appl. No.: 09/646,067
(22) PCT Filed: Mar. 12, 1999
(86) PCT No.: PCT/DE99/00693
§ 371 (c)(1),
(2), (4) Date: Nov. 27, 2000
(87) PCT Pub. No.: WO99/47914
PCT Pub. Date: Sep. 23, 1999

(30) Foreign Application Priority Data

Mar. 14, 1998 (DE) .......................... 198 11 150

(51) Int. Cl.$^7$ ............................. G01N 21/84
(52) U.S. Cl. .................. 422/82.05; 422/70; 422/82.08; 422/82.09; 422/82.11
(58) Field of Search ............... 422/70, 82.05, 422/82.08, 82.09, 82.11

(56) References Cited

U.S. PATENT DOCUMENTS

| | | | |
|---|---|---|---|
| 3,600,099 A | * | 8/1971 | Schoeffel |
| 3,746,869 A | | 7/1973 | Lindstedt et al. |
| 6,008,888 A | * | 12/1999 | Nottke et al. |

FOREIGN PATENT DOCUMENTS

| | | |
|---|---|---|
| DE | 2047 952 | 4/1972 |
| DE | 32 47 355 A1 | 6/1984 |
| DE | 41 33 131 C1 | 2/1993 |
| DE | 4433 305 A1 | 4/1996 |
| EP | 0 060 709 B1 | 9/1982 |
| EP | 0 457 526 A2 | 11/1991 |
| EP | 0 669 515 A3 | 8/1995 |
| FR | 2 661 986 A1 | 11/1991 |
| JP | 06333125 | 12/1994 |
| WO | 93/14392 | 7/1993 |

OTHER PUBLICATIONS

International Search Report dated Jul. 15, 1999, PCT/DE98/00693.

(List continued on next page.)

*Primary Examiner*—Jan Ludlow
(74) *Attorney, Agent, or Firm*—Baker & Daniels (57) ABSTRACT

The invention relates to a thin-layer chromatography apparatus (1) having a plurality of optical light guides to inject light from a light source (2) onto a thin-layer plate (4) and to feed light from the thin-layer plate to an optical examining device (6). To obtain a robust, compact thin-layer chromatography apparatus having a high spectral and spatial resolution, with which there are only minimal disturbances, if any, caused by ambient light and which is nonetheless economical to produce, the invention provides for the emitted-light guides (3) and or received-light guides (5) to be positioned in a regular geometrical pattern in relation to each other either towards or away from the plate, as represented by the rows (11 and 14). The light spots emitted by the emitted-light guides and the field of vision of the received-light guide overlap in an adjustable manner (linear movements 12b, pivoting movements 12a), as regards spatial resolution and light yield. A thin-layer plate (4) which is oriented in a planar manner by reference measurement and has a chromatography path (10) is displaced by a control unit (7) in relation to the light guides (8) which are at a distance of a few 100 μm and is examined (6) and evaluated (7) by spectroscopy for fluorescence, reflectance and/or absorption.

25 Claims, 3 Drawing Sheets

OTHER PUBLICATIONS

Quantitative Evaluation of Chromatograms from Totally Illuminated Thin–layer Chromatographic Plates by Irena Vovk and Mirko Prosek, Journal of Chromatography A, 768 (1997) 329–333.

Development of a system for Measuring the UV Spectra of Components Separated by TLC, Siegfried Ebel and Wolfgang Windmann, Journal of Planar Chromatography, vol. 4, Mar./Apr. 1991, psg. 171–173.

Fiber Optic Fluorescence Scanning in Thin–layer Chromatography, A. Navas Diaz and F. Garcia Sanchez, Instrumentation Science & Technology, 22(3), 273–281 (1994).

Fibre–Optic Remote Sensor fir In Situ Fluorimetric Quantification in Thin–layer Chromatography, A. Navas Diaz, Analytica Chimica Acta, 255 (1991) 297–303.

Determination of Reflectance of Pesticide Spots on Thin–layer Chromatograms Using Fiber Optics, Merton Beroza and K. R. Hill, Analytical Chemistry, 28, 1550 (1956).

A Versatile Spectrophotometric Scanner for Large TLC Plates, Bette L. Hamman and Malcolm M. Martin, Analytical Biochemistry 15, 305–312 (1966).

Spectral Detection in Thin–layer Chromatography by Linear Photodiode Array Spectrometry, S. Bayerbach and G. Gauglitz, Analytical Chemistry (1989) 335:370–374.

Vollautomatische, rechnergesteuerte Auswertung von Dunnschicht–Chromatogrammen, S. Ebel, E. Geitz and J. Hocke, GIT FAchz. Lab. 24 Jg. 7/80.

Remissionsspektren: Moglichkeiten und Grenzen, Wolfgang Windmann, Wurzburg(1991), pp. 1–3, 140–151.

* cited by examiner

THIN-LAYER CHROMATOGRAPHY APPARATUS

The present invention relates to a thin-layer chromatography apparatus according to the generic term of claim 1.

Thin-layer chromatography is a widespread process for the separation and analysis of substance mixtures. There, a stationary phase is provided as a thin layer on a suitable carrier made of glass, polyester, aluminum or the like. The substance mixture to be investigated is applied at a starting point or a starting line on the stationary phase. The thin-layer plate is then developed. For this a mobile phase is brought as eluant (Eluens) onto the starting line or the starting point, say by placing the thin-layer plate in a trough chamber from where the mobile phase begins-to run, especially by the capillary action of the stationary phase on the thin-layer. The mobile phase there can carry along over the thin-layer plate constituents of the substance mixture to be investigated and that are soluble in that phase. The less-well-soluble components remain on the stationary phase. If the individual components of the applied substance mixture, by reason of substance-specific retention values, show different distributions between mobile and stationary phase, this leads to a breaking-up of the substance mixture over the thin-layer plate. There is obtained a spatial distribution of the components over the thin-layer plate that is substance-specific. The analysis of the distribution pattern, therefore of a chromatogram, makes possible qualitative and quantitative statements about the components of the substance mixture.

The required analysis of the developed thin-layer chromatography plates occurs ordinarily optically with thin-layer chromatography apparatuses, in which the thin-layer plate is irradiated with light, and with which it is possible to investigate how the irradiated light is altered by the thin-layer plate.

The present invention concerns itself more precisely with such an optical thin-layer chromatography apparatus, and it is not relevant whether the application and development proper of the thin-layer plate also occur in the apparatus itself; further, it is insignificant whether the carrier is rigid or flexibly formed from glass, polyester or the like, so long as it is accessible to an optical investigation of the developed chromatogram.

The optical determination as to which substances are present in the chromatogram can be supported, on the one hand, by the place which a certain component of the substance mixture has reached on the thin-layer plate in the development, and, on the other hand, by its optical properties, i.e. the absorption capacity of the substance, its fluorescent properties, etc. An exact investigation requires, therefore, both a high local resolution and also an exact spectral investigation.

It has been proposed ("Development of a system for measuring the UV spectra of components separated by TLC" by S. Ebel and W. Windmann in J. Planar Chromatography, 1991, pp. 171 ff), to conduct light from a deuterium lamp over a fiber-optic bundle onto a thin-layer plate and to feed it from there to a photo diode array detector. The fiber-optic bundle consists of a "Y" fiber which is used to conduct the light of the deuterium lamp onto the thin-layer plate, and to conduct it from there to the optical examination arrangement.

Measures with such systems are described in a large number of publications, for example A. N. Diaz and F. Garcia Sanchez in "Fiber optic fluorescence scanning in thin-layer chromatography" in "Instrumentation Science and Technology, 22 (3), 273–281 (1994)"; A. N. Diaz "Fiber-optic remote sensor for in situ fluorimetric quantification in thin-layer chromatography" in Analytica Chimica Acta, 255 (1991) 297–303.

A further device is known from "Determination of Reflectance of Pesticide Spots on Thin-Layer chromatograms Using Fiber Optica" by M. Beroza, K. R. Hill and K. H. Norris in Analytical Chemistry, vol. 40, 1608–1613 (1968). There it is proposed to scan a thin-layer plate with stochastically arranged Y-light conductors. The foot of the Y-fibers is led to the thin-layer plate, its first arm to a light source and its other arm to an optical investigation device. A reading head is required for the plate scanning and a head for the reference measurement on an adjacent free path.

In the article "A versatile Spectrophotometric Scanner for Large TLC Plates" by B. L. Hamman and M. L. Martin in Analytical biochemistry vol. 15, 305–312 (1966) it is proposed to install in a light-proof housing a plate scanner which comprises a driven slide piece, with which a fiber bundle is moved over a thin-layer plate. Sending and receiving photo-conductors are arranged facing one another lying opposite on the slide piece. The light spot size can be determined by the sliding of slots of suitable size in front of the sending photo-conductor.

A problem with such thin-layer chromatography apparatuses lies in the uneven distribution of the substances over the regions to which they are carried on the thin-layer plate during the development. The concentration is highest in the center of a zone and decreases toward the edges of the spot.

A known possibility for avoiding such faults lies in illuminating a large spot. In a further known arrangement (S. Bayerbach and G. Gaulitz "Spectral detection in thin-layer chromatography by linear photo diode array spectrometry" in Fresenius Z. Anal. Chem. (1989) 335:370–374) there is proposed, therefore a light spot size of one to two millimeters dependent on the distance from the thin-layer plate. This takes place also in use of unordered fiber light bundles.

It was further proposed (S. Ebel, E. Geitz and J. Hocke in "Fully automatic, computer-controlled evaluation of thin-layer chromatograms" in GIT Fachz. Lab, 24th year, pp. 660 ff) to lead the light spot in meander pattern over the substance spots on the thin-layer plate. It has further been proposed to deflect the thin-layer plate by a definite amount over an eccenter?, in order to avoid the point-form measuring of a thin-layer chromatogram spot, cf. vol. 5 "D ünnshicht-chromatographie" of Ullmans encyclopedia of technical chemistry.

What is disadvantageous with the previously described measurements by means of which the uneven substance distribution over the spot is supposed to be compensated for, is regularly the reduced local resolution. It leads with a given amount of substance to a worsened separating performance, or with limited amounts of substance to worsened detection sensitivity.

From WO 93/14392 there is known an analysis device with a polychromatic light source. The light source can comprise a glow lamp light source with a small opening or, preferably, a semiconductor light source, for example an LED.

From EP 0 060 709 B1 there is known a process and a device for multidimensional real-time chromatography. The prior known system has first means for the chromatographic separating of a sample of an unknown composition into a first grouping of components, in which these first means can be a matter of a chromatographic thin-layer plate; second means for the further separating of the components mentioned into a higher-dimensional second group of components; third means for the recognizing of the components mentioned. The third means can be a linear multi-photodiode array which detects how a light source illuminates the eluting solvent on the thin-layer plate. The illumination can use a plurality of light sources which are used successively and emit at different wavelengths that are specific for the unknown components sought. The publication concerns itself also with the problem that the analysis is not very accurate because of the spreading of the spots. The known process proposes the real-time investigation during the separation, but allows there in particular no subsequent evaluation of already developed thin-layer plates. It is therewith not possible to draw upon the prior-known system for the investigation of filed thin-layer plates, as required, say, for the documentation of charge qualities in the pharmaceutical industry.

The dissertation "Remission spectra: Possibilities and limits" von W. Windmann (University of Würzburg, 1991) concerns itself with the use of light conductors in thin-layer chromatography apparatuses. It is stated (page 144) that it is absolutely necessary to achieve high intensities of the irradiated light on the thin-layer plate in order to obtain a sufficiently strong remission signal, that, on the other hand however, the spot size must be sufficiently large so that a spot on its path is still perceived if the chromatographic development has faults. The use of larger fiber bundles (allegedly) can solve these problems only within narrow limits.

A device in which a large number of coherent parallel light beams is used in order to determine the position of an object is known from EP 0 669 515 A3. The known device is used in order to determine the position of tree trunks or other long stretched-out objects in a channel or the like.

The present invention aims to make new information available for industrial use and, in particular, but not exclusively to make ready a sturdy, compact thin-layer chromatography apparatus with high spectral and local resolution, in which also in particular in any case slight disturbances arise through ambient light and which is nevertheless economical to manufacture.

The solution of the aim set is claimed independently; Preferred forms of execution are found in the dependent claims.

A basic thought of the invention lies therefore in arranging the light conductors in a predetermined geometric alignment.

Therewith there is obtained first of all a regular, preferably uniform illumination or detection over the spot width by a plurality of light conductors. It is thus possible directly to achieve a desired light intensity distribution over the entire substance spot. The alteration of the irradiated light by absorption and/or fluorescence can then likewise be detected over the entire spot width. The sliding-in of blinds for the achievement of a desired illumination and scanning geometry is not absolutely required.

The geometric arrangement of the sending and receiving light conductors to one another makes it possible purposefully to influence the overlapping of the coverage of the light spot from a sending-light conductor with the coverage that is detected by the receiving-light conductors and to make it controllable according to wish. The regularity of the arrangement which is conditioned by the fact that sending and receiving light conductors are also geometrically arranged among one another, provides that the overlapping integrals of different sending and receiving conductors allocated to one another correspond, which holds also if for certain purposes not all the overlapping integrals are exactly identical to one another, but groups of corresponding overlapping integrals are present, say in the case of use of several different types of fibers. The local resolution is determined in the proposed arrangement by the comparatively small overlapping integral and not by the spot size of the entire illuminated thin-layer plate zone.

Coverage fields of the receiving-light conductors and light spots of the sending-light conductors can adjustably partially overlap, it being possible to adjust the distance of the light conductors from the thin-layer plate, this being possibly done by piezoelectric modulation or with mechanical means.

Preferably at least ten—generally however clearly more—sending-light conductors are provided, which are arranged linearly closely adjacent to one another. The light spots of in each case adjacent sending-light conductors on the thin-layer plate can nearly overlap or be slightly spaced from one another. In this case a receiving-light conductor preferably receives light from at least two sending-light conductors.

With two or more parallel series of sending-light conductors next to one another a given plate is more intensely illuminated and by lighting from different sides the angular distribution of the received light becomes more uniform. If light of different spectral intensity is irradiated in each case into different light conductors there is yielded on the thin-layer plate a desired, say nearly uniform illumination spectrum simply by arrangement of the particular light conductors. The illumination with parallel light conductors makes it possible moreover to irradiate light perpendicularly onto the plate and to collect the light remitted perpendicularly to the plate for evaluation. This is advantageous according to the Lambert cosine law for the achievement of high light intensities.

The series are movable with respect to one another for the adjustment of the light-spot overlapping of the sending-light conductors of different series, say by swing and/or translation of one series toward the other or away from this.

An adjustably variable spacing of the sending-light conductors within a series makes possible measurements with different overlappings of the light spots with one another or with particular coverages and therewith different local resolutions.

Input-side-coupling of light from different light sources into the sending-light conductors facilitates the obtaining of a desired illumination spectrum. An intensity approximately uniform over the spectral range used ensures that the detectors used in the optical investigation apparatus used are not overloaded by especially intense signals in narrow spectral ranges. A desired illumination spectrum is possible to achieve also with a single light source by means of dispersive elements between light source and thin-layer plate, or by light conductors of different length.

A refractive lens as dispersive element improves, moreover, the coupling efficiency into the sending-light conductors. The coupling efficiency is also increased if a possibly present fiber mantle on the lamp side is removed, possibly detached away, and the ends of several fibers are possibly welded or cast in synthetic resin. For an especially uniform illumination of the thin-layer plate with at least nearly the same intensity over all the sending light conductors, between light source and input side of the sending light conductors there is arranged a diffusing screen or the like.

While it is advantageous per se to provide a plurality of optical-sending light conductors, preferably also or at least a plurality of optical reception light conductors is provided, such as at least twenty, preferably, however, between 50 and 100 receiving light conductors.

The plurality of optical receiving- light conductors can be arranged for simultaneous reception of light transmitted through the thin-layer plate and of light remitted from the thin-layer plate or from the substances presented on the thin-layer plate. Also if light is simultaneously received, in each case optical investigation arrangements of their own are not absolutely necessary. Economically, the receiving-light conductors provided for the remission/fluorescence and transmission are led to one and the same optical investigation device and evaluated there in alternation. For this the light path between optical investigation apparatus and thin-layer plate can be partitioned off in selective alternation, say by means of a chopper, or the light conductors are coupled in alternation into the optical investigation apparatus. Therewith there takes place a quasi-simultaneous evaluation.

An especially preferred variant of the thin-layer chromatography apparatus has at least one series of sending-light conductors and one series (row) of receiving-light conductors, preferably with light conductors arranged tightly each over 10 thick, next to one another.

If only a single row of sending-light conductors and receiving light conductors is formed, sending-light conductors and receiving-light conductors can be arranged in common on Y-fibers ending on the thin-layer chromatography plate or in alternation in one row. While with the use of Y-fibers a 100% overlapping of sending-light spots and receiving viewing fields is given, this will not be the case with sending- and receiving-light conductors arranged in one row, which is advantageous if through a smaller overlapping integral an increased local resolution is sought. The overlapping integral can be influenced especially by the spacing between light conductor ends and the thin-layer plate.

When sending-light conductors radiate light of different spectral intensity, each receiving light conductor receives light. This improves the optical evaluation by the investigation apparatus.

The sending- and receiving-light conductors can be arranged in different parallel rows, in which case an offset arrangement "on the gap" (auf Lücke") between sending- and receiving-light conductor row is preferred, in order to achieve a better light yield. An equal diameter for all the sending- and receiving-light conductors is not absolutely necessary there, which, if need be, makes possible a tighter packing.

Also different materials are usable, say quartz fiber for the detection of ultraviolet light, and teflon fibers for the range above 250 nm.

If so desired, the light-conductor arrangement can be arranged into a broad broom, in which 30 fibers each with a 100 $\mu$ diameter yield a broom width of about 3.5 mm, and 50 fibers yield already 5.5 mm. On the edges a shading can be performed, if this is too much for a given thin-layer plate, say because of only small amounts of material. For this at will the coupling of light into the outer sending-light conductors can be suppressed at the light source, the radiation at the plate, radiation of light into the receiving-light conductors and/or the coupling of light from the receiving-light conductors into the optical investigation apparatus.

Sending- and receiving-light conductors are preferably moved with a step motor or the like relatively to the thin-layer plate, in order to scan a chromatography path. Preferably in the case of a rigid scanning head the plate is moved. This avoids changes of the light transmission in the light conductors through movement-conditioned refraction index variations, say on bending.

The orientation of the thin-layer plate is visually documented with a CCD camera or the like.

Also a means can be provided for the detection and/or for the compensation of non-plane-parallel lying thin-layer plates. For the determination of the plate alignment, the distance of the sending and/or scanning head from the plate, at points of the plate not affected by solvent and substance, can be determined with reference measurements as white standard. Such points are to be found, for example, behind the eluting running end of the outer paths, or to the side of the outer paths. The reference measurement can determine, say, the entire light intensity in reflection. If the intensity of the reflected light on the different separate points is not equal, then the plate does not lie parallel. A previously executed measurement can then be rejected or a measurement still being carried out is suppressed. What is important above all is an oblique position which simulates (or fakes) differences from path to path, since typically the analysis occurs by comparison with substances running on adjacent paths. An oblique position leading to differences within a path practically causes no trouble with such measurements, but can nevertheless easily be balanced out. The sending- and or receiving- light conductors in the present arrangement for the obtaining of small sending light spots and therewith of high local resolution can thereby be led close to the plate; ordinarily distances are clearly under one millimeter, such as a few 100 $\mu$. The correction prevents the situation that through oblique positions such as could be caused by grains of sand or the like under the thin-layer plate, measurement errors could arise.

The invention is described in the following only by way of example with the aid of the drawing. In this drawing.

Figure 1:
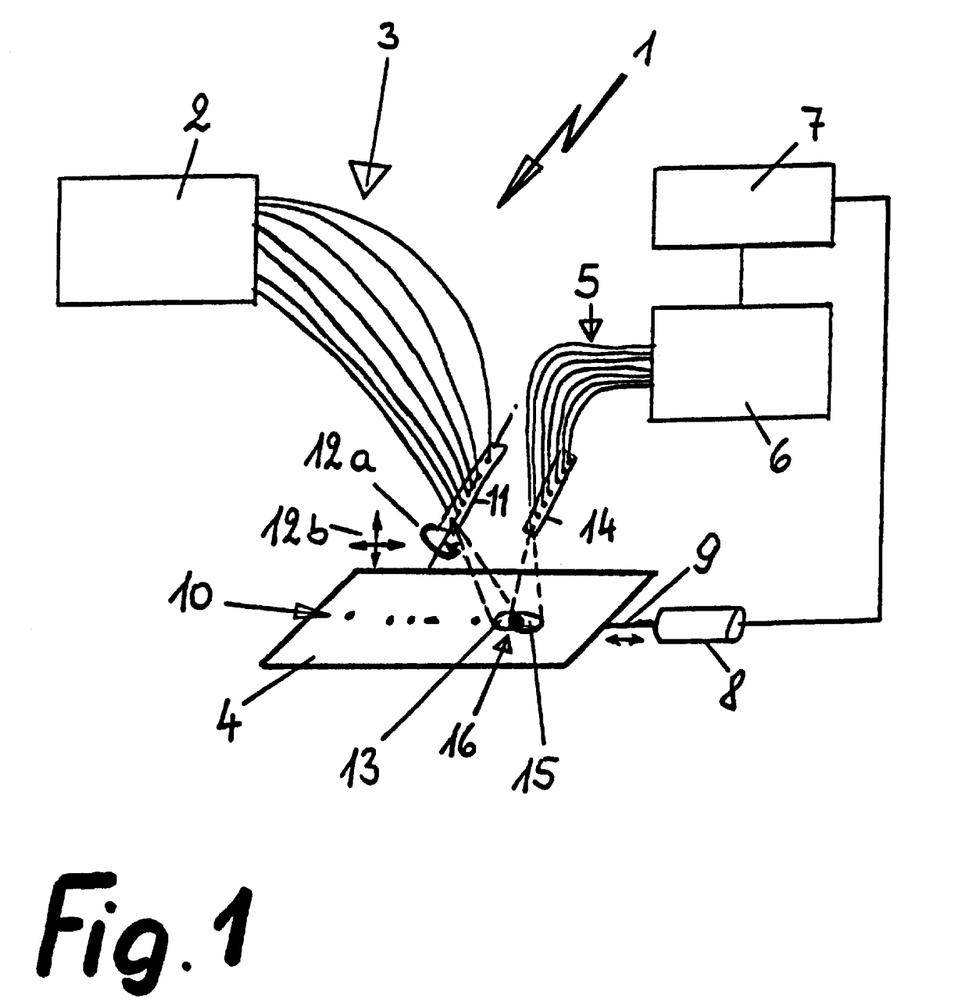
FIG. 1 shows a thin-layer chromatography apparatus according to the present invention.

According to FIG. 1 a thin-layer chromatography apparatus designated generally with 1 compares a light source 2, to which there are coupled a large number of optical fibers 3 as sending-light conductors in order to guide the light onto a developed thin-layer plate 4. The sending-light conductors 3 cast a sending light spot 13 onto the thin-layer plate 4 which, uniformly illuminated, extends over the entire width of a chromatography path 10. Receiving-light conductors 5 are arranged in like manner with the thin-layer plate. The reception coverage field 15 of the receiving-light conductors 5 overlaps at least partially with the sending-light spot 13, as indicated by the darkened area 16 that represents the overlapping integral, so that the coverage field 15 detects reflected remission and/or fluorescence light. The receiving-light conductors 5 lead to an optical investigation apparatus 6, which is connected with a central control and data-processing unit 7. The control- and data-processing unit 7 controls an electric shifting unit 8, such as a step motor, with which the thin-layer plate 4 can be moved relatively to the sending- and receiving-light conductors 3 and 5 in such manner that a chromatography path 10 is moved under the light conductors 3 and 5, respectively. The movement of the thin-layer plate 4 occurs preferably by means of a step motor 8 or the like controlled by a (sc. device) 7 such as a PC.

With the light source 2 it can be a matter of a deuterium lamp, a tungsten lamp, a combined deuterium-and-tungsten lamp (translucent lamp), a wide-band high pressure lamp, a narrow-band, a low-pressure lamp, a pulsed- or continuous-dash laser, for example an excimer laser, a metal vapor laser, an Nd-YAG laser, variable-frequency lasers such as ring lasers, also harmonically frequency-multipled, and the like. In the beam path between light source and light-coupling ends of the sending-light conductors 3 there can be provided filters such as narrow-band interference filters, band-pass filters, edge filters and the like, as well as lenses for the raising of the coupling efficiency and/or diffusion screens for the uniform illumination of all the sending-light conductors 3.

As sending-light conductors 3 there come into consideration quartz fibers, teflon fibers or conventional glass fibers. The use of light conductors transparent also in the broad ultraviolet range is advantageous. Light conductors can be used with a diameter of, for example, 50 $\mu$ to 200 $\mu$, in which, for the generation of small light spots on the thin-layer chromatography plate, with consequently better local resolution, small photoconductor diameters are preferred. The light conductors, however, do not necessarily have to be round.

If sheathed fibers are used as sending-light conductors 3, it is possible to etch away the fiber mantles at the light-source end, and to weld the fiber ends for better utilization of the lamp intensity, say by means of a laser, or to cast them in transparent synthetic resin such as epoxy resin. If a diffusion screen is mounted in front of such an arrangement there is achieved a uniform illumination of all the fibers and therewith an at least nearly constant illumination of the thin-layer plate over the path width.

At the outlet end of the sending light conductors 3 the fibers can be provided, if need be, with cylindrical lenses with focal lengths of, for example about 2.5 mm, Fresnel lenses or the like, insofar as the dispersion yielded in the use of lenses does not cause trouble, and that a special light pattern on the thin-layer plate is desired. If so desired, the fiber ends can also be ground round or pointed or used in a conventional manner as section or breakage edge without further measures. Likewise conceivable is the polishing or the like of the fiber ends.

The sending-light conductor-fiber ends are preferably arranged adjacently in a row several millimeters wide and fixed in a support 11 which is swingable about its longitudinal axis according to arrow 12a and movable according to arrows 12b perpendicularly to the thin-layer plate and parallel in its direction toward the receiving light row. Shifting of the sending-light conductor row parallel to the thin-layer plate, and/or swinging of the sending-light conductor row about the longitudinal axis (arrow 12a) alters the overlapping integral 16. The receiving-light conductor row can be a fixed one.

If so desired, there is provided on the support 11 a device with which the distance of the sending-light conductors 3 from one another in the row can be adjusted (not shown). Because of the small required stroke, a piezoelectric modulator is usable for this. In this manner the width of the illuminated path can be adjusted.

While in the drawing, for reasons of representation, the distances represented between the thin-layer plate and the sending-and receiving-light conductors nearly correspond to the typical thin-layer plate dimensions, the distance apart of the sending-and/or reading head in practice will be only a few 100 $\mu$ in height over the thin-layer plate.

In practice a larger number of light conductors in a row, as represented, is preferred. The particular number in a row amounts, for example, to 50 to 100 light conductors. Although the principle of the present invention can also be carried out with a small number of light conductors, such as 5 to 10, a very large number of light conductors is preferred in order to make it possible analytically to scan the extremes (edge ?) traces with strong light broad line application. The broad line application of the starting substances yields correspondingly broad substance bands on the thin-layer plate.

The thin-layer plate 4 is a pre-developed thin-layer plate or a thin-player plate developed in the thin-layer chromatography apparatus of the present invention. The use of other carrier materials for the mobile phase besides plates, say flexible carriers, is likewise conceivable but is subsumed for the present purposes under the concept thin-layer plate.

The receiving light conductors 5 are arranged next to one another in a row in a fixing device 14, in which the spacing of the fibers from one another is, if necessary, likewise adjustable as desired. Insofar as the adjustment of the fiber spacing occurs, say, piezoelectrically modulated, the spacing can be adjusted, for example by the control 7.

In the preferred form of execution the diameter of the receiving-light conductor 5 is less than the diameter of the sending light conductor 3. With the same light-conductor materials the receiving-light spot is smaller than the sending light spot and the coupling-in of interfering light is still further reduced, which improves the signal-to-noise ratio, although already with identical diameters for sending and receiving-light conductors there takes place such a good residual light suppression that the thin-layer chromatography apparatus can be operated without blacking-out in normal use.

The sending-light conductors 3 lead to the optical investigation arrangement 6, with which it can be a matter of a spectrometer to which the receiving-light conductors are coupled next to one another in such manner that they illuminate the entry gap uniformly and without loss, without aperture blind or the like. As required, light conductors can be mounted directly over a dispersive element, such as a prism, if, for example, UV lenses, expensive and frequently troublesome by reflections on the boundary layer, are to be avoided.

A fixed light-conductor geometry at the spectrometer gap and on the thin-layer plate requires merely an unrepeated and thus a time-saving adjustment but nevertheless allows, through the high reproducibility and the good coupling-in efficiency, signal resolutions or more than 14 bits with conventional optical investigation apparatuses. On the spectrometer, a diode line (Diodenzeile) or the like is preferred, in particular a photon-counting CCD arrangement, in order to scan the complete spectrum simultaneously.

The thin-layer chromatography apparatus is operated as follows:

First of all the thin-layer plate is fully developed. Then the thin layer- plate 4 is laid into the thin-layer chromatography apparatus.

In the event that an optical adjustment is desired, the overlapping integral can be adjusted by swinging the row 11 and shifting the rows 11 and 14. The swinging perpendicularly against the plate is kept so small that according to the Lambert cosine law no relevant intensity losses occur. The overlapping is set for the desired local resolution: The stronger the overlapping is, the lower the local resolution is, but the utilization efficiency of the light radiated in rises. Shifting unit 8 is moved into the home position.

The light source 2 is then excited. Light passes through the sending-light conductors 3 in the form of a narrow, brightly illuminated slot onto the thin-layer plate 4, where it illuminates the width of a whole chromatography path 10. If necessary, first still the total intensity of the light reflected from the thin-layer plate is measured at distant points, not touched by solvents and the like. If the white light reference thus obtained is equal in those points, the thin-layer plate 4 lies flat. Instead of the white light reference, also a reference to certain spectral components is possible.

The separated substance mixture on the chromatography path 10 absorbs light in some points in certain spectral ranges and it fluoresces in other spectral ranges. The light altered in this way, which is radiated from the thin-layer plate passes at least in part into receiving light conductor 5, since the sending-light spots and the reception coverage fields overlap adjustably.

The light radiated into the receiving-light conductors 5 is led through the receiving-light conductors to the optical investigation apparatus and there it is resolved into its spectral components. When the spectrum in the spectrometer is detected with a diode line, a rapid exposure (Aufnahme) of the complete spectrum is possible.

In this way a three-dimensional parameter field can be obtained for the chromatogram, in which wavelength, absorption or fluorescence and extent along the chromatography path represent the three parameters. Through the broad, slot-type illumination of the whole path, errors through measurement at the faulty location, transversely to the path are avoided as long as the broom is sufficiently wide.

The data are read by the control and processing unit 7 over a corresponding signal electronic system. The evaluation is possible at the actual time or later, for which purpose preferably raw data are stored, say the light intensities.

As soon as a spectrum is received in one place, the step motor 8 is energized in order to move the thin-layer plate 4 defined amount further. The displacement is determined there according to the resolution (sigma) which is to be expected in each case for a given investigation both from the thin-layer plate development and also from the optical arrangement. It is preferred in the case of a resolution of say 100 $\mu$ (4 T) to perform a shift by say 50 $\mu$. At typical development running heights of 50 mm there are yielded 1000 spectra per path. Since through the good background suppression the measuring times can be chosen short, there is thus possible an exposure time per path within ca. 60 sec. or less.

After shifting of the thin-layer plate a new spectrum is received. This continues until the end of the course that is until the end of the thin-layer plate is reached. Then a further path, possibly in reverse direction, can be scanned.

If so desired, then in supplement the alignment of the thin-layer plate in the thin-layer chromatography apparatus can be recorded, for example, with a CCD camera, then documented.

Thanks to the broad, uniformly illuminated range over which the sending light conductors emit, an exact and therefore expensive angular alignment of the thin-layer plate is not required. Rather, in the case of thin-layer plates laid obliquely into the thin-layer chromatography apparatus, a track following the exact running direction can be established in the subsequent data analysis.

While in the preceding two separate sending- and receiving-light conductor rows are provided, this is not absolutely necessary and it is also possible to chose other light conductor arrangements. Moreover, it is also possible to arrange one of the sending- and receiving- light conductors above the thin-layer plate, and the other underneath the thin-layer plate, in order to determine the absorption produced by the separated substance mixture.

While in the preceding example the thin-layer plate was shifted along its running path direction in order to record the spectrum of a single path, this is not absolutely required. Rather, the plate can also be examined transversely to its running direction, especially if, instead of a qualitative analysis. a quantitative determination of a known substance with known running series is to occur in a large number of samples. In this measurement, therefore, several substance samples are brought in X-direction adjacently onto the plate and developed in Y-direction orthogonal hereto, so that there is yielded a mixture splitting in Y-direction. Now the running distance of the substance to be determined is found, that is to say the Y-coordinate up to which the different samples applied adjacently in X-direction have run. The sending- and receiving- light conductor row is placed on this Y-position and moved in X-direction over all the running paths of the various samples. This is then especially advantageous because the evaluation with a thin-layer chromatography scanner presents one of the most time-consuming processes of the whole analysis if a large number of running paths have to be evaluated. The high time expenditure can be considerably reduced by the simultaneous or nearly simultaneous evaluation of only a very short section of many running paths. The invention makes such an evaluation possible, since the sending- and receiving-light rows have a greater extent than the same spot on the individual running path. Also, with this application an exact adjustment is not required. A utilization especially in the beverage industry, say for the determination of the caffeine content of soft drinks is directly possible by quantitative thin-layer chromatography.

Further sending and receiving-light conductor arrangements are described now with reference to FIGS. 2 to 12. It is obvious that these light conductor arrangements can be used in a thin-layer chromatography apparatus as described generally above.

In FIGS. 2 to 12 the symbol "X" stands in each case for a sending-light conductor, while the symbol "0" stands in each case for a receiving light conductor. For better visualization the number of light conductors is smaller than preferred in practice. In a discerning manner sending-and receiving-light conductors, especially with arrangement in different rows, can be held and fixed in common at will or, as shown in FIG. 1, held and fixed separately.

As a consequence, the different light conductor arrangements have different local resolutions as well as different utilization efficiencies of the radiated light. The different expected local resolutions for fibers of the diameter 100 $\mu$, and the yield expected with the particular arrangement through maximal overlapping of sending- and receiving-light spots, are given in the table appearing below.

Figure 2:
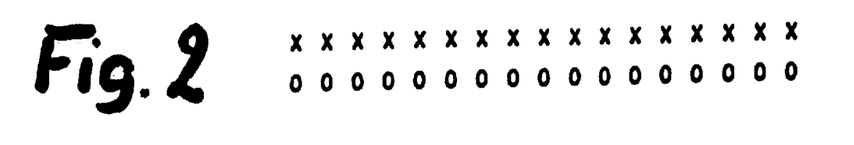
FIGS. 2 to 14 show preferred arrangements of sending-light conductors "IX" and of receiving light conductors "o".

According to FIG. 2 sending- and receiving- light conductors are always arranged adjacently to one another.

Figure 3:
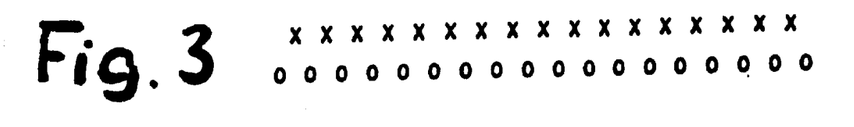

According to FIG. 3 sending- and receiving-conductor rows are offset against one another, and stand, therefore, on a gap. (auf Lücke)

Figure 4:
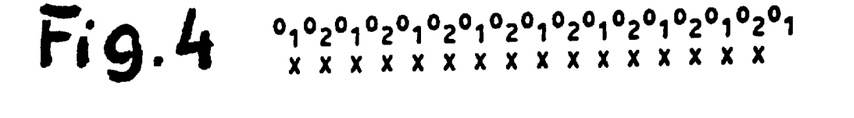

According to FIG. 4 over continuously equal sending light conductors X light is fed over different light conductors or to different parts of an optical investigation apparatus; for example, two spectrometers can be provided with different spectral sensitivity.

Figure 5:
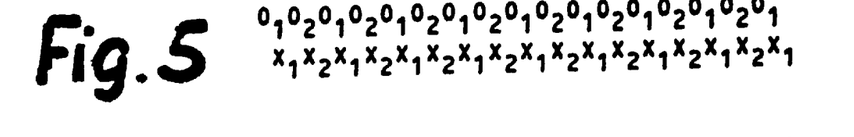

FIG. 5 corresponds largely to FIG. 4, but the to the sending-light conductors $X_1$ light is fed from a first light source and to the sending light conductors $X_2$ light is fed from a second light source. In this manner a desired illumination spectrum can be obtained.

Figure 6:
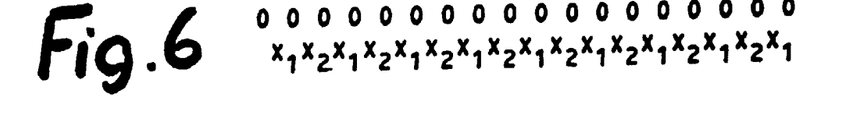

FIG. 6 largely corresponds to FIG. 5, but all the receiving light dividers are equal and lead to the same spectrometer.

Figure 7:
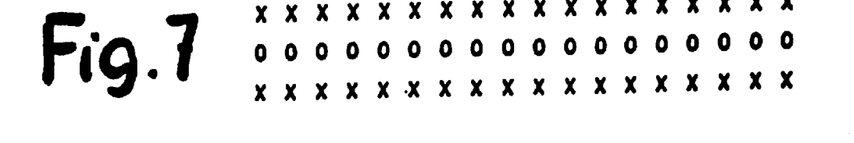

FIG. 7 shows an arrangement in which a row of receiving-light conductors is arranged between two sending-light rows. Analogously there would be possible the arrangement of one sending-light row between two receiving-light rows, and this would be advantageous for fluorescence measurements because of a light yield of virtually 100% with a local resolution of 200 $\mu$ with fibers of 100 $\mu$.

Figure 8:
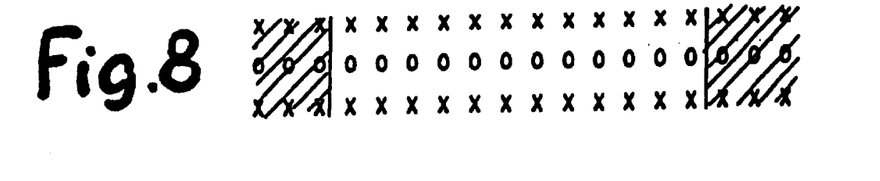

FIG. 8 shows by way of example that by shading-off of the outer border zones of the arrangement of FIG. 7 the width over which the thin-layer plate is scanned can be reduced.

Instead of this or in addition to this, parallel-arranged sending- and receiving-light rows can be shifted in the row direction against one another so that in each case the outer light conductors are unpaired. Accordingly, at one end excessive sending- light conductors are present and at the other end excessive receiving-light conductors are present and the effective broom width is reduced to the middle broom range, where paired light conductors are still present.

Figure 9:
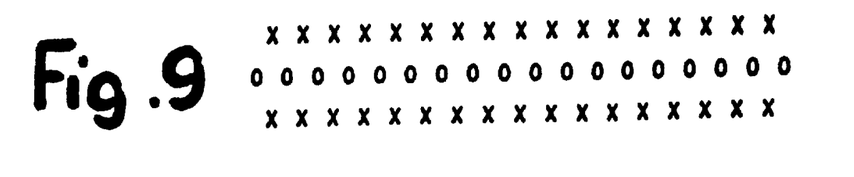

FIG. 9 corresponds largely to the arrangement of FIG. 7, but sending- and receiving-light conductors are set against one another over a gap.

Figure 10:
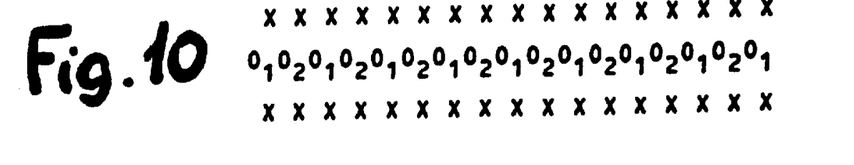
Figure 11:
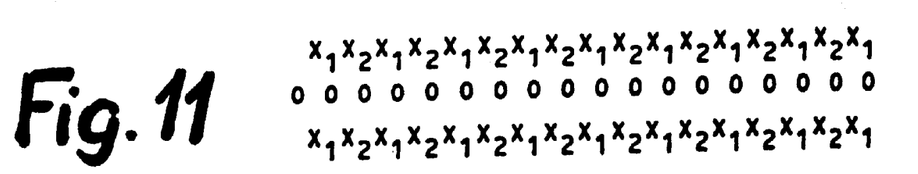
Figure 12:
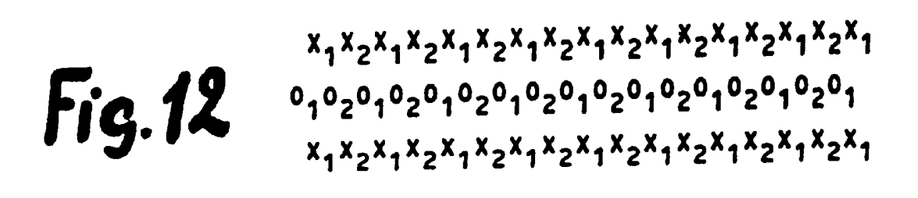

FIGS. 10 to 12 show how light from different sources can be coupled into sending-light conductors, and how these light sources can be led in alternation to different optical investigation arrangements.

Figure 13:
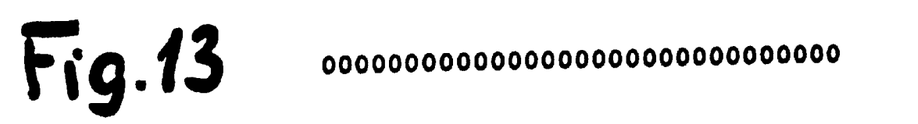

According to FIG. 13, Y-fibers are used.

Figure 14:
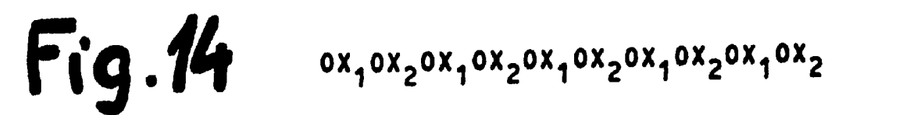

FIG. 14 shows the alternating arrangement of sending and receiving light conductors in a row next to one another. Here too it is possible to radiate light from two lamps simultaneously onto the thin-layer plate and/or to feed light to different investigation arrangements.

With the arrangements there are yielded different optical properties as follows:

| Arrangement according to Figure | Local resolution on the thin-later plate (estimated) [$\mu$] | Light yield (estimated) [%] |
|---|---|---|
| FIG. 2 | 90 | 33 |
| FIG. 3 | 105 | 35 |
| FIG. 4 | 90 | 33 |
| FIG. 5 | 90 | 33 |
| FIG. 6 | 90 | 33 |
| FIG. 7 | 200 | 100 |
| FIG. 9 | 190 | 100 |
| FIG. 10 | 190 | 100 |
| FIG. 11 | 190 | 100 |
| FIG. 12 | 190 | 100 |
| FIG. 14 | 190 | 100 |
| FIG. 15 | 160 | 36 |

There was described, accordingly, a rapid, automatic thin-layer chromatography apparatus, with which by multi-wave detection there is possible a checking of the separating cleanness, which makes possible a validation of the separating system. By the fixed light-conductor geometry of the described apparatus there are largely eliminated the problems of adjusting and also dispersive corrections and the like are no longer required. The local resolution can be adjusted individually in a simple manner, simply by altering the distance of the light conductor from the thin-layer plate, and in particular it is possible to measure simultaneously in remission transmission and in fluorescence. There the system, thanks to the elimination of lens systems, is economical, makes possible a modular construction, is compact, and allows the evaluation of line- and point-form application as well as a subsequent background correction at different wavelengths without renewed measuring.

With the arrangement described it is possible to represent a thin-layer chromatography path three-dimensionally, namely with respect to the x-y position on the thin-layer plate as well as its spectral properties (third dimension).

What is claimed is:

1. A thin-layer chromatography apparatus comprising:
   a plurality of aligned optical sending-light conductors for irradiation of light onto a thin-layer plate and producing conductor light spots thereon; and
   a plurality of aligned optical receiving-light conductors for receiving and feeding light from reception fields on the thin-layer plate to an optical investigation apparatus,
   said sending-light conductor light spots and said reception fields atbeast partially overlap,
   said apparatus further comprising an overlapping integral adjusting means for adjusting an integral by which said sending-light spots and said reception fields overlap.

2. A thin-layer chromatography apparatus according to claim 1, wherein the overlapping integral adjusting means adjusts at least one of a distance between the light-conductors and a distance between the light-conductors and the thin-layer plate.

3. A thin-layer chromatography apparatus according to claim 1, wherein the plurality of aligned optical sending-light conductors is at least 10 and the sending-light conductors are arrayed closely together linearly so that the light spots of adjacent sending-light conductors are spaced apart less than a coverage diameter of the receiving-light conductors.

4. A thin-layer chromatography apparatus awarding to claim 3, wherein at least two generally parallel sending-light conductor rows are provided, the light spots of which are spaced on the thin-layer plate less than the coverage diameter of a receiving light conductor.

5. A thin-layer chromatography apparatus according to claim 1, wherein a distance between the sending-light conductors is adjustable.

6. A thin-layer chromatography apparatus according to claim 5, wherein a piezoelectric modulator is used to adjust the distance between the sending-light conductors.

7. A thin-layer chromatography apparatus according to claim 1, further comprising a coupling-in device at an input side coupling-in of light from at least two different light sources of definite spectral intensity into the sending-light conductors.

8. A thin-layer chromatography apparatus according to claim 7, wherein in at least one of light sources, the coupling-in device and the sending-light conductors are configured so that light of different spectral intensity is emitted onto the thin-layer plate.

9. A thin-layer chromatography apparatus according to claim 8, further comprising at least one dispersive element selected from the group consisting of a cut-off filter, a band pass filter, a coupling-in lens, and coupling-out lens, said dispersive element configured to effect at least one of influence of the spectral distribution of light and raising of the coupling-in efficiency.

10. A thin-layer chromatography apparatus according to claim 1, wherein the plurality of receiving-light conductors comprises at least 20 receiving-light conductors which are aligned in an array.

11. A thin-layer chronography apparatus according to claim 10, wherein the receiving-light conductors are arranged for the simultaneous reception of transmitted and remitted irradiation with at least one receiving-light conductor row above and below the thin-layer plate.

12. A thin-layer chromatography apparatus according to claim 10, wherein the plurality of receiving-light conductors comprises between 50 and 100 receiving-light conductors.

13. A thin-layer chromatography apparatus according to claim 1, in which the sending-light conductors and the receiving-light conductors are arranged in at least one common row.

14. A thin-layer chromatography apparatus according to claim 1, wherein sending-light conductors and receiving-light conductors form a common row connected to Y-fibers ending on the thin-layer plate and alternating sending-light and receiving light conductors.

15. A thin-layer chromatography apparatus according to claim 1, wherein the sending-light and receiving-light conductors are arranged in parallel rows with a receiving-light conductor row between a pair of sending-light conductor rows.

16. A thin-layer chromatography apparatus according to claim 15, wherein the receiving-light conductor row between the pair of sending-light conductor rows is offset from these rows.

17. A thin-layer chromatography apparatus according to claim 15, wherein the receiving-light conductor row between the pair of sending-light conductor rows, and the pair of sending-light conductor rows face one another on both sides of the thin-layer plate.

18. A thin-layer chromatography apparatus according to claim 1, wherein a sending-light conductor row is arranged between two receiving-light conductor rows, and the optical investigation arrangement comprises means for measuring fluorescence.

19. A thin-layer chromatography apparatus according to claim 1, wherein the sending-light and receiving-light conductors have different diameters.

20. A thin-layer chromatography apparatus according to claim 19, wherein the diameters of receiving-light conductors are larger than the diameters of the sending-light conductors.

21. A thin-layer chromatography apparatus according to claim 1, further comprise an adjusting device for reducing the number of one of the sending-light conductors and the receiving-light conductors used.

22. A thin-layer chromatography apparatus according to claim 1, further comprising a step motor for moving the sending-light and receiving-light conductors relative to the thin-layer plate.

23. A thin-layer chromatography apparatus according to claim 22, wherein the step motor moves the sending-light and receiving-light conductors together.

24. A thin-layer chromatography apparatus according to claim 1, further comprising a CCD camera for monitoring adjustment of the thin-layer plate.

25. A thin-layer chromatography apparatus awarding to claim 1, further comprising means for at least one of determining and aligning of thin-layer plates that are misaligned.

* * * * *

UNITED STATES PATENT AND TRADEMARK OFFICE
CERTIFICATE OF CORRECTION

PATENT NO.   : 6,485,687 B1
DATED        : November 26, 2002
INVENTOR(S)  : Spangenberg et al.

Page 1 of 1

It is certified that error appears in the above-identified patent and that said Letters Patent is hereby corrected as shown below:

<u>Column 12,</u>
Line 11, delete "atbeast"
Line 17, delete "at least one of"
Line 17, after "between" insert -- at least one of --
Line 57, delete "chronography" and substitute -- chromatography --

<u>Column 14,</u>
Line 7, delete "comprise" and substitute -- comprising --
Line 22, delete "awarding" and substitute -- according --

Signed and Sealed this

Fourth Day of March, 2003

JAMES E. ROGAN
*Director of the United States Patent and Trademark Office*